United States Patent
Desai et al.

(10) Patent No.: US 6,777,003 B1
(45) Date of Patent: Aug. 17, 2004

(54) IODINE COMPLEX OF ALKYL POLYGLYCOSIDES

(75) Inventors: Suresh Desai, Wayne, NJ (US); John Frederick Hessel, Metuchen, NJ (US)

(73) Assignee: Cognis Corporation, Cincinnati, OH (US)

( * ) Notice: Subject to any disclaimer, the term of this patent is extended or adjusted under 35 U.S.C. 154(b) by 1826 days.

(21) Appl. No.: 08/482,579

(22) Filed: Jun. 7, 1995

(51) Int. Cl.$^7$ .......................... A01N 59/12; A61K 33/18
(52) U.S. Cl. ...................... 424/670; 424/667; 424/669; 424/671; 424/672; 514/777; 514/772; 422/29; 422/37
(58) Field of Search ................. 424/667, 669, 424/670–672; 514/772, 777; 422/29, 37

(56) References Cited

U.S. PATENT DOCUMENTS

| | | | |
|---|---|---|---|
| 4,576,818 A | 3/1986 | Shetty | 424/672 |
| 5,109,127 A | 4/1992 | Sekiguchi et al. | 536/115 |
| 5,174,927 A | 12/1992 | Honsa | 252/543 |
| 5,190,747 A | 3/1993 | Sekiguchi et al. | 424/56 |
| 5,223,179 A | 6/1993 | Connor et al. | 252/548 |
| 5,266,690 A | 11/1993 | McCurry, Jr. et al. | 536/18.6 |
| 5,310,542 A | 5/1994 | Au et al. | 424/52 |
| 5,332,528 A | 7/1994 | Pan et al. | 252/548 |
| 5,338,491 A | 8/1994 | Connor et al. | 252/548 |
| 5,352,387 A | 10/1994 | Rahman et al. | 252/548 |
| 5,358,656 A | 10/1994 | Humphreys et al. | 252/174 |
| 5,885,620 A * | 3/1999 | Foret | 424/669 |
| 6,153,229 A * | 11/2000 | Foret | 424/669 |

FOREIGN PATENT DOCUMENTS

| | | |
|---|---|---|
| EP | 0550280 | 12/1992 |
| EP | 0550279 | 7/1993 |
| EP | 0550281 | 7/1993 |

OTHER PUBLICATIONS

Lennette et al. (eds.), Manual of Clinical Microbiology, 4$^{th}$ ed., American Society for Microbiology, Washington, DC, 1985, p. 132.

* cited by examiner

*Primary Examiner*—John Pak
(74) *Attorney, Agent, or Firm*—Aaron R. Ettelman; Steven J Trzaska

(57) ABSTRACT

An iodine complex concentrate containing (a) from about 0.5 to about 30% by weight of iodine; (b) from about 0.2 to about 14% by weight of an iodide component selected from the group consisting of iodide salt, iodide acid and mixtures thereof; and (c) from about 2% to about 85% by weight of a nonionic sugar surfactant selected from the group consisting of alkyl glucose esters, aldobionamides, gluconamides, glyceramides, glyceroglycolipids, polygydroxy fatty acid amides, alkyl polyglycosides having the general formula I:

$$R_1O(R_2O)_b(Z)_a \qquad \text{I}$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6, and mixtures thereof, all weights being based on the weight of the concentrate.

22 Claims, No Drawings

IODINE COMPLEX OF ALKYL POLYGLYCOSIDES

FIELD OF THE INVENTION

The present invention generally relates to a novel concentrate containing complexed iodine. More particularly, the present invention relates to an iodine complex concentrate for use in antimicrobial use compositions.

BACKGROUND OF THE INVENTION

Iodine compositions have long been known to impart desirable antimicrobial and non-staining characteristics. Complexed iodine compositions are known to be useful as sanitizers for elements ranging from contact surfaces and glassware to plant formulation facilities. An especially important application for iodine compositions is in clean-in-place (CIP) systems. CIP systems are generally found in industries which produce fluidized ingestible products for humans or animals such as the dairy industry, the pharmaceutical industry, and the food industry. Clean-in-place systems are generally regarded as large production plant systems having reservoirs, pipes, pumps and mixing vessels which cannot be broken down to be cleaned. Additionally, clean-in-place preparation systems often require high sanitization when used in the production of ingestible substances.

In order to be dependable and useful to an end user, iodine compositions must be stable (i.e. remain homogeneous) over a wide range of temperature and prolonged periods of time. If stability is lost, and the products separate, the utility of the composition is significantly degraded and they can present a potential hazard to the user. Generally speaking, stability in this context means that a given product must remain completely homogeneous after extended storage at temperatures ranging from room temperature to as high as 40° C., which can occur during transport in closed vehicles. Furthermore, although a given product may separate when frozen, especially after undergoing several freeze-thaw cycles, it must be readily reconstitutable as a homogeneous mixture upon simple shaking or mixing.

Iodine-based antimicrobial use products designed for topical application to the skin are normally formulated with a certain amount of emollient. The most common emollients employed are glycerin, lanolin and its derivatives, sorbitol, fatty acid esters of polyhydroxylated compounds and propylene glycol. These emollients are used at levels ranging from below 1% to as much as 10% in use compositions. Glycerin is the most widely used emollient in bovine teat dips and is also used extensively at low levels in human topical detergent-iodine and povidone-iodine formulations. Emollients are needed because of the harshness to skin associated with those surfactants contained in the detergent part of the composition.

Another desirable functional charactersitic for iodine-based antimicrobial use compositions designed for topical application is the ability to spread evenly on the skin and not drain off so rapidly as to prevent insufficient germicidal contact time. Many of the usual ingredients in antimicrobial products contribute to viscosity. However, it is common for topical products to be formulated with a specific thickener to provide added viscosity. There are many viscosity modifiers compatible with iodine-based antimicrobial use systems, such as carboxymethylcellulose derivatives, polyacrylate derivatives, alginates, xanthates and polysaccharides. These are typically used at levels below 1% by weight in a final use composition. These types of ingredients, properly selected, have an insignificant effect on the homogeneity of a given use composition. On the other hand, where dilutable concentrates are desired, viscosity-modifying additives can become a problem and special care must be taken in the selection of specific agents and their levels of use in concentrates.

The prior art is replete with examples of antimicrobial use formulations having relatively high detergent/average available iodine ratios in excess of 5:1. There are, however, a number of potential advantages associated with the use of very low detergent/average available iodine ratios in germicidal iodine concentrates and use compositions designed for skin or tissue application. For example, in a low ratio product of this type, there would be less organic matter to react with the iodine, thereby rendering such compositions more stable relative to the normal high ratio of detergent to average available iodine content. Another advantage is that reduced amounts of detergent would be expected to be less irritating to the skin and would accordingly require a lesser amount of emollient. Compositions with lower detergent/average available iodine ratios could be formulated to have higher, and more stable, free or uncomplexed iodine levels. The use of minimal amounts of detergent also would allow for the possibility of reduced water content in concentrates, thereby correspondingly reducing packaging, shipment and storage costs. However, one obvious disadvantage associated with these types of formulations is that lower amounts of detergent component reduce the detersive effectiveness of the germicidal composition. Moreover, the use of lower ratios of detergent/average available iodine also results in the composition becoming less storage stable which makes them significantly less marketable.

Accordingly, it is an object of the present invention to provide iodine complex concentrate designed for topical applications onto both human and animal skin that employs a component acting as both a complexing agent for the iodine, and a mild yet effectively detersive surfactant which is less harsh on skin and tissue, thereby requiring the addition of little if any emollients to the antimicrobial use composition.

It is another object of the present invention to provide an iodine complex concentrate for use in antimicrobial use compositions to disinfect and sanitize various contact surfaces including those present in CIP systems, as well as glassware which is capable of being employed at relativley high detergent/average available iodine ratios, thus making the formulated antimicrobial compositions more storage stable over prolonged time periods and temperature ranges while imparting maximum detersive properties.

SUMMARY OF THE INVENTION

The present invention overcomes the problems outlined above by providing a stable iodine complex concentrate for use in various aqueous antimicrobial use compositions. Accordingly, the present invention provides an iodine complex concentrate containing:

(a) from about 0.5 to about 30% by weight of iodine;

(b) from about 0.2 to about 14% by weight of a component selected from the group consisting of iodide salt, iodide acid and mixtures thereof; and (c) from about 2.0 to about 85% by weight of a nonionic sugar surfactant selected from the group consisting of alkyl glucose esters, aldobionamides, gluconamides, glyceramides, glyceroglycolipids, polyhydroxy fatty acid amides, alkyl polyglycosides having the general formula I:

$$R_1O(R_2O)_b(Z)_a \qquad I$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6, and mixtures thereof, all weights being based on the weight of the concentrate.

The present invention also provides an aqueous antimicrobial use composition containing the above-disclosed iodine complex concentrate and a diluent.

The present invention also provides a process for cleaning, disinfecting and sanitizing an intended surface involving contacting the intended surface with the above-disclosed aqueous antimicrobial use composition.

DESCRIPTION OF THE INVENTION

Other than in the operating examples, or where otherwise indicated, all numbers expressing quantities of ingredients or reaction conditions used herein are to be understood as modified in all instances by the term "about".

The foregoing and other related objects are achieved, and the disadvantages of the prior art are obviated by the surprising discovery that a nonionic sugar surfactant effectively functions as both a complexing agent for iodine in iodine complex concentrates and a mild, yet detersive surfactant when the iodine complex concentrates are diluted to form an aqueous antimicrobial use composition. The term nonionic sugar surfactant as used herein refers to surfactants that are based on saccharide moieties. The nonionic sugar surfactants which may be employed in the present invention are selected from the group consisting of alkyl polyglycosides, alkyl glucose esters, aldobionamides, gluconamides, glyceramides, glyceroglycolipids, polyhydroxy fatty acid amides, and mixtures thereof.

Preferred alkyl polyglycosides which can be used as the complexing agent in the concentrate of the invention have the formula I:

$$R_1O(R_2O)_b(Z)_a \qquad I$$

wherein Z is a glucose residue and b is zero. Such alkyl polyglycosides are commercially available, for example, as GLUCOPON®, or PLANTAREN® surfactants from Henkel Corporation, Ambler, Pa., 19002. Examples of such surfactants include but are not limited to:

1. GLUCOPON® 225 Surfactant—an alkyl polyglycoside in which the alkyl group contains 8 to 10 carbon atoms and having an average degree of polymerization of 1.7.
2. GLUCOPON® 425 Surfactant—an alkyl polyglycoside in which the alkyl group contains 8 to 16 carbon atoms and having an average degree of polymerization of 1.6.
3. GLUCOPON® 625 Surfactant—an alkyl polyglycoside in which the alkyl groups contains 12 to 16 carbon atoms and having an average degree of polymerization of 1.6.
4. APG® 325 Surfactant—an alkyl polyglycoside in which the alkyl groups contains 9 to 11 carbon atoms and having an average degree of polymerization of 1.6.
5. GLUCOPON® 600 Surfactant—an alkyl polyglycoside in which the alkyl groups contains 12 to 16 carbon atoms and having an average degree of polymerization of 1.4.
6. PLANTAREN® 2000 Surfactant—a $C_{8-18}$ alkyl polyglycoside in which the alkyl group contains 8 to 16 carbon atoms and having an average degree of polymerization of 1.4.
7. PLANTAREN® 1300 Surfactant—a $C_{12-16}$ alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which and the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated. The alkyl polyglycoside of the present invention acts as the complexing agent for the iodine complex concentrate.

The alkyl glucose ester sugar surfactants are generally disclosed in U.S. Pat. Nos. 5,109,127 and 5,190,747 the entire contents of both of which are incorporated herein by reference. These sugar surfactants have the general formula II:

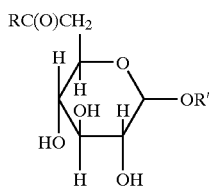

wherein R represents a fatty acid residue of 6 to 20 carbon atoms, preferably 6 to 12 carbon atoms and $R^1$ represents an alkyl group having 2 to 6 carbon atoms. Representative examples of such alkyl glucose esters are 1-ethyl-6-caprylglucoside, 1-ethyl-6-laurylglucoside, 1-butyl-6-caprylglucoside, 1-ethyl-6-palmitylglucoside and 1-ethyl-6-oleylglucoside.

The aldobionamide sugar surfactants are generally disclosed in U.S. Pat. No. 5,310,542 and in published European Patent Application No. 550,281 both of which are incorporated herein by reference. An Aldobionamide is generally defined as the amide of an aldobionic acid or aldobionolactone and an aldobionic acid in turn is defined as a sugar substance (e.g. any cyclic sugar) in which the aldehyde group has been replaced by a carboxylic acid which upon drying is capable of cyclizing to form an aldonolactone. The aldobionamides can be based on compounds comprising two saccharide units, e.g. lactobionamides, maltobionamides, cellobionamides, melibionamides, or gentiobionamides, or they can be based on compounds comprising more than two saccharide units provided that the polysaccharide has a terminal sugar unit with an aldehyde group available.

The preferred aldobionamides of the present invention are lactobionamides of the formula III:

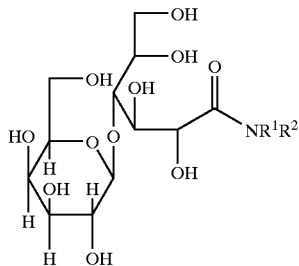

wherein $R^1$ and $R^2$ are the same or different and are selected from hydrogen and an aliphatic hydrocarbon radical containing up to about 36 carbon atoms (e.g. alkyl groups and alkenyl groups which groups may also include a heteroatom such as N, O, S, present, for instance, as an amide, carboxy, ether and/or saccharide moiety) except that $R^1$ and $R^2$ cannot simultaneously be hydrogen. The aliphatic hydrocarbon radical preferably contains up to 24 carbon atoms, most preferably from 8 to 18 carbon atoms. Representative examples of such lactobionamides are N-propyl lactobionamide, N-pentyl lactobionamide, N-decyl lactobionamide, N-hexadecyl lactobionamide, N-oleyl lactobionamide, N-dodecyl-N-methyl lactobionamide, and N-dodecyloxypropyl lactobionamide.

The gluconamide sugar surfactants are generally disclosed in U.S. Pat. No. 5,352,386 the entire contents of which is incorporated herein by reference. These surfactants have the general formula IV:

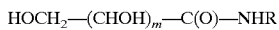

wherein m is an integer from 2 to 5; and R is a straight or branched, saturated or unsaturated aliphatic hydrocarbon having 4 to about 24 carbon atoms, preferably 8 to 24 carbon atoms, which R group can also contain a heteroatom selected from the group consisting of oxygen, nitrogen and sulfur. Representative examples of such cosurfactants are N-octylerythronamide, N-decylerythronamide, N-dodecylerythronamide, N-tetradecylerythronamide, N-decylxylonamide and N-dodecylxylonamide.

The glyceramide sugar surfactants are generally disclosed in U.S. Pat. No. 5,352,387 the entire contents of which is incorporated herein by reference. These cosurfactants have the general formula V:

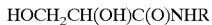

wherein R is a $C_8$ to $C_{24}$ straight or branched chained, saturated or unsaturated aliphatic hydrocarbon in which the R group may also be substituted by a heteroatom selected from oxygen, nitrogen and sulfur. Representative examples of such cosurfactants are N-octylglyceramide, N-decylglyceramide and N-hexadecylglyceramide.

The glyceroglycolipid sugar surfactants are generally disclosed in U.S. Pat. No. 5,358,656, and published European Patent Application No. 550,279 the disclosure of each of which is incorporated herein by reference. The glyceroglycolipids can be of the formula VI:

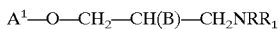

wherein $A^1$ is a saccharide, preferably having one or more saccharide units, more preferably a mono or disaccharide and most preferably a monosaccharide such as glucose or galactose; R and $R_1$ are the same or different and are hydrogen, a branched or unbranched hydrocarbon radical having from 1 to about 24, preferably from about 6 to about 18 carbon atoms; B is OH or a $NR^2R^3$ group, wherein $R^2$ and $R^3$ may be the same or different and are hydrogen, a branched or unbranched hydrocarbon radical having 1 to 24, preferably from 6 to 18 carbon atoms, and $NRR_1$ and B are positionally interchangeable. Representative examples of such cosurfactants are 3-(butylamino)-2-hydroxypropyl-β-D-galactopyranoside, 3-(octylamino)-2-hydroxypropyl-β-D-galactopyranoside, 3-(eicosylamino)-2-hydroxypropyl-β-D-galactopyranoside, 3-(butylamino)-2-hydroxypropyl-β-D-glucopyranoside, and 3-(pentylamino)-2-hydroxypropyl-β-D-mannopyranoside.

Other glyceroglycolipid surfactants are disclosed in published European Patent Application No. 550,280 which is incorporated herein by reference. These cosurfactants are of the formula VII:

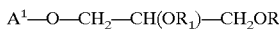

wherein $A^1$ is from 1 to 4 saccharide units and more preferably represents a mono or disaccharide, and most preferably a monosaccharide, for example, glucose or galactose; R and $R_1$ are the same or different and are hydrogen, or a branched or unbranched, saturated or unsaturated, hydrocarbon radical having from 1 to 24 carbon atoms, preferably from 6 to 18 carbon atoms. Representative examples of such cosurfactants are 3-(butyloxy)-2-hydroxypropyl-β-D-galactopyranoside, 3-(eicosyloxy)-2-hydroxypropyl-βD-galactopyranoside, 3-(decyloxy)-2-hydroxypropyl-β-D-galactopyranoside, 3-(butyloxy)-2-hydroxypropyl-β-D-glucopyranoside, 3-(octyloxy)-2-hydroxypropyl-β-D-mannopyranoside, 3-(tetradecyloxy)-2-hydroxypropyl-β-D-lactoside, 3-(octadecyloxy)-2-hydroxypropyl-β-D-maltoside, 3-(octyloxy)-2-hydroxypropyl-β-D-galactotrioside, and 3-(dodecyloxy)-2-hydroxypropyl-β-D-cellotrioside.

The polyhydroxy fatty acid amide sugar surfactants are generally disclosed in U.S. Pat. Nos. 5,174,927, 5,223,179 and 5,332,528 the entire disclosure of each of which is incorporated herein by reference. The polyhydroxy fatty acid amide surfactant component of the present invention comprises compounds of the structural formula VIII:

wherein: $R^1$ is H, $C_1$–$C_4$ hydrocarbyl, 2-hydroxy ethyl, 2-hydroxy propyl or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl, preferably straight chain $C_7$–$C_{18}$ alkyl or alkenyl, more preferably straight chain $C_8$–$C_{17}$ alkyl or alkenyl, most preferably straight chain $C_{11}$–$C_{17}$ alkyl or alkenyl, or mixture thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)n$-$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic or aliphatic monosaccharide, and alkoxylated derivatives thereof. Most preferred are glycityls wherein n is 4, particularly —$CH_2$—$(CHOH)_4$—$CH_2OH$.

In the above Formula $R^1$ can be, for example, N-methyl, N-ethyl, N-propyl, N-isopropyl, N-butyl, N-2-hydroxy ethyl, or N-2-hydroxy propyl.

$R^2C(O)N<$ can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Representative examples of such surfactants are N-methyl-N-1-deoxyglucityl cocoamide and N-methyl-N-1-deoxyglucityl tallowamide.

Other suitable polyhydroxy fatty acid amide surfactants (see U.S. Pat. Nos. 5,223,179 and 5,338,491, the entire contents of each which are incorporated herein by reference) are those of the formula IX:

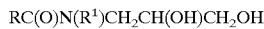
$RC(O)N(R^1)CH_2CH(OH)CH_2OH$ wherein R is a $C_7$–$C_{21}$ hydrocarbyl species, i.e. coconut, tallow, palm fatty alkyl and oleyl, and $R^1$ is a $C_1$ to $C_6$ hydrocarbyl or substituted hydrocarbyl species, i.e. N-alkyl-N-(1,2-propanediol) and N-hydroxyalkyl-N-1,2-propane diol fatty acid amides. Representative examples of such cosurfactants are the tallow amide of 3-[2-(hydroxyethyl) amino]-1,2-propanediol (HEAPD), the palmitate amide of 3-methylamino-1,2-propanediol (MAPD) and the lauramide of MAPD.

The function of the iodine in the present invention is to provide disinfecting and sanitizing antimicrobial efficacy. Iodine is generally chosen over other elemental disinfecting and sanitizing agents due to its high antimicrobial efficacy over short periods of time.

Iodine is a nonmetallic element belonging to the halogen family in Group VIIA of the periodic table. It is the heaviest common member of this family and the only one that is solid at ambient temperatures. Iodine, like other halogens, is very active chemically, but more desirable than other halogens as being less violent in its action. Iodine is slightly solube in water, the solubility increasing with temperature. Iodine also dissolves in many organic solvents.

The iodine component of the present invention is derived from two sources, i.e., from both iodine itself and an iodide constituent such as sodium iodide, potassium iodide or hydroiodic acid, and, optionally, water. Generally, the amount of available iodine present in the iodine complex concentrate of the invention ranges from about 200 to about 20,000 ppm iodine. Also, the weight ratio of nonionic sugar surfactant acting as complexing agent to available iodine in the concentrate ranges from about 6:1 to about 1:1, respectively, and is preferably about 4:1.

In a preferred embodiment of the present invention, the iodine complex concentrate of the present invention contains from about 5 to about 20% by weight of iodine, from about 0.2 to about 14% by weight of iodide salt, and from about 2.0 to about 85% by weight of an alkyl polglycoside having the general formula I:

$R_1O(R_2O)_b(Z)_a$      I wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6, and mixtures thereof, all weights being based on the weight of the concentrate. It should also be noted that the formed iodine complex concentrate of the present invention may be either in liquid or solid, i.e., powder, form.

The iodine complex concentrate of the present invention may be diluted with a diluent such as water to form an aqueous antimicrobial use composition. Aqueous antimicrobial use compositions are well known in the art and are employed for a variety of uses such as in clean-in-place (CIP) systems used in industries which produce fluidized ingestible products for humans or animals such as the dairy industry, the pharmaceutical industry and the food industry, to clean contact surfaces and glassware. Aqueous antimicrobial compositions are also well known for their use in topical skin applications to clean, disinfect and sanitize both human and animal skin. Topical aqueous antimicrobial use compositions are primarily used as pre-operative antiseptic preparations, hand cleaners and in bovine teat dips for mastitis prevention.

Thus, the present invention provides an antimicrobial use composition resulting from the dilution of the iodine complex concentrate of the present invention to an available iodine content level of from about 0.5 to about 200 ppm iodine. The diluent employed is typically water, although any other type of desirable diluent may also be used. Similarly, the specific amount of diluent to be employed will depend on the particular use of the antimicrobial use composition. In general, however, the amount of diluent used should be sufficient to form an antimicrobial use composition having an available iodine content level of from about 0.5 to about 200 ppm iodine, as stated above. It should also be noted that while the nonionic sugar surfactant primarily acts as a complexing agent for iodine, it also acts as a detersive surfactant. Thus, if it is desired to enhance the cleaning efficacy of an aqueous antimicrobial use composition, additional surfactants may also be employed in the formulation of either the iodine complex concentrate or the aqueous antimicrobial use composition. Examples of suitable surfactants include anionics, nonionics, cationics, amphoterics, zwitterionics and mixtures thereof. Additional additives may also be employed when formulating either the iodine complex concentrate or the aqueous antimicrobial use composition such as fragrances, dyes, fillers, viscosity modifiers, foam regulators or additional complexing agents.

The present invention also provides a process for cleaning, disinfecting and sanitizing various intended surfaces. Examples of intended surfaces include both human and animal skin, as well as contact surfaces such as those present in clean-in-place (CIP) systems used to produce fluidized ingestible products as well as glassware. In general, however, any surface which requires cleaning, disinfecting and sanitizing qualifies as an intended surface. The process involves contacting the intended surface with the above-described aqueous antimicrobial use composition.

The present invention will be better understood from the examples which follow, all of which are intended to be illustrative only and not meant to unduly limit the scope of the invention. Unless otherwise indicated, percentages are on a weight-by-weight basis.

EXAMPLE 1

An iodine complex concentrate composition was prepared having the following formulation.

|     | Component         | %/wt  |
| --- | ----------------- | ----- |
| (a) | GLUCOPON ® 325    | 79.0  |
| (b) | NaI               | 6.8   |
| (c) | Iodine (crystals) | 14.2  |
|     |                   | 100.0 |

NaI was added to the alkyl polyglycoside with stirring and the mixture was then stirred for an additional 25 minutes. The iodine crystals were then added to the mixture in increments with stirring, and then this mixture was stirred for an additional 4 hours at room temperature. The mixture was then heated to from is 35 to 40° C. and held at that temperature for approximately 30 minutes with stirring to form the iodine complex concentrate composition.

EXAMPLE 2

An iodine complex concentrate composition was prepared as in Example 1 having the following formulation.

|     | Component         | %/wt  |
| --- | ----------------- | ----- |
| (a) | GLUCOPON ® 425    | 83.8  |
| (b) | NaI               | 5.2   |
| (c) | Iodine (crystals) | 11.0  |
|     |                   | 100.0 |

EXAMPLE 3

An iodine complex concentrate composition was prepared as in Example 1 having the following formulation.

|     | Component         | %/wt  |
| --- | ----------------- | ----- |
| (a) | GLUCOPON ® 600    | 60.6  |
| (b) | NaI               | 5.2   |
| (c) | Iodine (crystals) | 11.0  |
| (d) | Deionized water   | 23.2  |
|     |                   | 100.0 |

EXAMPLE 4

An iodine complex concentrate composition was prepared as in Example 1 having the following formulation.

|     | Component         | %/wt  |
| --- | ----------------- | ----- |
| (a) | GLUCOPON ® 225    | 47.0  |
| (b) | NaI               | 5.2   |
| (c) | Iodine (crystals) | 11.0  |
| (d) | Deionized water   | 36.8  |
|     |                   | 100.0 |

Table 1 summarizes the initial iodine content of the Examples at a temperature of 25° C.

TABLE 1

| Exs. | AI at 25° | TI at 25° | Theor. value AI | Theor. value TI | % yield Iodine AI | % yield Iodine TI |
| ---- | --------- | --------- | --------------- | --------------- | ----------------- | ----------------- |
| 1    | 12.8      | 20.6      | 14.3            | 21              | 89.5              | 98.0              |
| 2    | 9.5       | 15.7      | 10.0            | 16.2            | 95.0              | 96.93             |
| 3    | 9.7       | 15.5      | 11.0            | 16.2            | 88.2              | 95.6              |
| 4    | 9.9       | 15.4      | 11.0            | 16.2            | 90.0              | 95.0              |
| C1*  | 21.2      | 27.2      | 22.0            | 31.0            | 96.3              | 88.1              |

*C1 = BIOPAL ® NR 20 a nonylphenoxy poly(ethylenoxy)-ethanol iodine complexing agent available from Rhone-Poulenc Cranbury, NJ 08512.
AI = available iodine
TI = total iodine Table 2 summarizes the iodine content of the Examples at a temperature of 25° C. and 50° C. after a storage period of 9 weeks.

TABLE 2

| Exs. | AI at 25°/50° | TI at 25°/50° | Theor. value AI | Theor. value TI | % yield Iodine AI | % yield Iodine TI |
| ---- | ------------- | ------------- | --------------- | --------------- | ----------------- | ----------------- |
| 1    | 13.0/12.3     | 21.0/20.8     | 14.3            | 21              | 90.9/86.0         | 100/99.0          |
| 2    | 9.4/8.7       | 15.7/16.1     | 10.0            | 16.2            | 94.0/87.0         | 97.0/99.3         |
| 3    | 9.7/12.1      | 16.0/21.0     | 11.0            | 16.2            | 88.2/---          | 98.7/---          |
| 4    | 10.0/9.3      | 15.7/15.8     | 11.0            | 16.2            | 90.9/84.5         | 97.0/97.5         |
| C1*  | 21.1/20.9     | 26.9/16.6     | 22.0            | 31.0            | 96.3/95.0         | 87.0/86           |

*C1 = BIOPAL ® NR 20 is a nonylphenoxy poly(ethlenoxy)-ethanol iodine complexing agent available from Rhone-Poulenc, Cranbury, NJ 08512.
AI = available iodine
TI = total iodine

EXAMPLE 5

An aqueous antimicrobial use formulation for topical skin application was prepared using the iodine complex concentrate prepared in Example 1 having the following formulation.

|     | Component             | %/wt |
| --- | --------------------- | ---- |
| (a) | Iodine complex of Ex. 1 | 18.4 |
| (b) | GLUCOPON ® 325        | 25.0 |

-continued

| | Component | %/wt |
|---|---|---|
| (c) | 70% H³PO₄ | 36.0 |
| (c) | Propylene Glycol | 8.0 |
| (d) | Deionized water | 12.6 |
| | | 100.0 |

Table 3 summarizes the stability results of Example 5 obtained after one week of storage, at a temperature of 25° C.

TABLE 3

| | Theoretical | Actual |
|---|---|---|
| AI | 2.43 | 2.44 |
| TI | 3.72 | 3.63 |

What is claimed is:

1. An iodine complex concentrate comprising:
   (a) from about 0.5 to about 30% by weight of iodine;
   (b) from about 0.2 to about 14% by weight of an iodide component selected from the group consisting of iodide salt, iodide acid and mixtures thereof; and
   (c) from about 2% to about 85% by weight of an alkyl polyglycoside having the formula I:

$$R_1O(R_2O)_b(Z)_a \qquad \text{I}$$

wherein $R^1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6, all weights being based on the weight of the concentrate.

2. The concentrate of claim 1 wherein said iodide salt is selected from the group consisting of sodium iodide, potassium iodide and mixtures thereof.

3. The concentrate of claim 1 wherein b of said general formula I is 0.

4. The concentrate of claim 1 having an available iodine content of from about 200 to about 20,000 ppm.

5. The concentrate of claim 1 wherein said component (a) is present in an amount of from about 5 to about 20% by weight, based on the weight of the concentrate.

6. The concentrate of claim 1 having a weight ratio of said component (c) to available iodine in said components (a)+(b) of from about 6:1 to about 1:1.

7. The concentrate of claim 6 wherein said weight ratio is 4:1.

8. The concentrate of claim 1 containing an additive selected from the group consisting of nonionics, anionics, cationics, amphoterics, zwitterionics, viscosity modifiers, fragrances, dyes, fillers, foam regulators, and mixtures thereof.

9. The concentrate of claim 1 having a pH of from about 2 to about 7.

10. An aqueous antimicrobial composition comprising an iodine complex concentrate and a diluent, said concentrate comprising:
    (a) from about 0.5 to about 30% by weight of iodine;
    (b) from about 0.2 to about 14% by weight of a component selected from the group consisting of iodide salt, iodide acid and mixtures thereof; and
    (c) from about 2% to about 85% by weight of an alkyl polyglycoside having the formula I:

$$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6, all weights being based on the weight of the concentrate.

11. The composition of claim 10 wherein said iodide salt is selected from the group consisting of sodium iodide, potassium iodide and mixtures thereof.

12. The composition of claim 10 wherein b of said general formula I is 0.

13. The composition of claim 10 having an available iodine content of from about 0.5 to about 200 ppm iodine.

14. The composition of claim 10 wherein said diluent is water.

15. The composition of claim 10 wherein said concentrate has a weight ratio of said component (c) to available iodine in said components (a)+(b) of from about 6:1 to about 1:1.

16. A process for cleaning, sanitizing and disinfecting an intended surface comprising contacting said intended surface with an aqueous antimicrobial composition containing an iodine complex concentrate and a diluent, said concentrate comprising:
    (a) from about 0.5 to about 30% by weight of iodine;
    (b) from about 0.2 to about 14% by weight of a component selected from the group consisting of iodide salt, iodide acid and mixtures thereof; and
    (c) from about 2% to about 85% by weight of an alkyl polyglycoside having the formula I:

$$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6, all weights being based on the weight of the concentrate.

17. The process of claim 16 wherein said iodide salt is selected from the group consisting of sodium iodide, potassium iodide and mixtures thereof.

18. The process of claim 16 wherein b of said general formula I is 0.

19. The process of claim 16 wherein said aqueous antimicrobial composition has an available iodine content of from about 0.5 to about 200 ppm iodine.

20. The process of claim 16 wherein said diluent is water.

21. The process of claim 16 wherein said intended surface is selected from the group consisting of human skin, animal skin, contact surfaces, and glassware.

22. The process of claim 16 wherein said concentrate has a weight ratio of said component (c) to available iodine in said components (a)+(b) of from about 6:1 to about 1:1.

* * * * *